United States Patent
Shouldice

(10) Patent No.: US 12,220,537 B2
(45) Date of Patent: *Feb. 11, 2025

(54) SYSTEMS, METHODS AND DEVICES FOR SMART HUMIDIFICATION

(71) Applicant: ResMed Sensor Technologies Limited, Dublin (IE)

(72) Inventor: Redmond Shouldice, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/400,087

(22) Filed: Dec. 29, 2023

(65) Prior Publication Data

US 2024/0131294 A1 Apr. 25, 2024

Related U.S. Application Data

(63) Continuation of application No. 17/772,198, filed as application No. PCT/IB2020/060245 on Oct. 30, 2020, now Pat. No. 11,872,350.

(Continued)

(51) Int. Cl.
*A61M 16/16* (2006.01)
*A61M 16/10* (2006.01)

(52) U.S. Cl.
CPC .......... *A61M 16/16* (2013.01); *A61M 16/107* (2014.02); *A61M 2205/33* (2013.01)

(58) Field of Classification Search
CPC .. A61M 16/16; A61M 16/161; A61M 16/024; A61M 16/105; A61M 16/1055;

(Continued)

(56) References Cited

U.S. PATENT DOCUMENTS

| 6,039,696 A | * | 3/2000 | Bell | A61M 16/08 128/204.21 |
| 7,997,270 B2 | * | 8/2011 | Meier | A61M 16/16 128/204.14 |

(Continued)

FOREIGN PATENT DOCUMENTS

| JP | H0618073 A | 1/1994 |
| JP | 2013526996 A | 6/2013 |

(Continued)

OTHER PUBLICATIONS

International Search Report and Written Opinion in International Application No. PCT/IB2020/060245, mailed Feb. 2, 2021 (15 pages).

*Primary Examiner* — Colin W Stuart
*Assistant Examiner* — Douglas Y Sul
(74) *Attorney, Agent, or Firm* — Nixon Peabody LLP

(57) ABSTRACT

Disclosed are methods, systems, and devices for providing a personalized humidification level. A control system receives, from a first sensor, one or more environmental parameters regarding conditions of the environment. The control system receives, from a second sensor, one or more physiological parameters associated with a user within the environment. The control system determines an action associated with a desired change in the humidity within the environment based, at least in part, on the one or more environmental parameters and the one or more physiological parameters. The control system causes, at least in part, a performance of the action associated with the change in the humidity in the environment based, at least in part, on moisture outputted by a humidifier module. The methods and devices perform the same functionality as the control system.

20 Claims, 8 Drawing Sheets

Related U.S. Application Data

(60) Provisional application No. 62/928,911, filed on Oct. 31, 2019.

(58) Field of Classification Search
CPC ............ A61M 16/106; A61M 16/1065; A61M 16/107; A61M 2205/33; A61M 2205/3368; A61M 2016/003
See application file for complete search history.

(56) References Cited

U.S. PATENT DOCUMENTS

| | | |
|---|---|---|
| 11,872,350 B2 * | 1/2024 | Shouldice ............ A61M 16/107 |
| 2008/0236577 A1 | 10/2008 | Power et al. |
| 2013/0087143 A1 | 4/2013 | Pujol |
| 2013/0104733 A1 | 5/2013 | Bangera et al. |
| 2014/0144438 A1 * | 5/2014 | Klasek ................. A61B 5/4812 |
| | | 128/203.14 |
| 2015/0128942 A1 * | 5/2015 | Tatkov ................... A61B 5/087 |
| | | 128/203.14 |
| 2016/0213879 A1 | 7/2016 | Parthasarathy et al. |
| 2017/0050056 A1 | 2/2017 | Xu et al. |
| 2019/0344038 A1 | 11/2019 | Novkov |

FOREIGN PATENT DOCUMENTS

| | | |
|---|---|---|
| JP | 2016176658 A | 10/2016 |
| JP | 2018536440 A | 12/2018 |
| WO | 2011151739 A1 | 12/2011 |
| WO | 2019131775 A1 | 7/2019 |

\* cited by examiner

SYSTEMS, METHODS AND DEVICES FOR SMART HUMIDIFICATION

CROSS-REFERENCE TO RELATED APPLICATION

This application is a continuation of U.S. application Ser. No. 17/772,198, filed on Apr. 27, 2022, now allowed, which is a U.S. National Stage of International Application No. PCT/IB2020/060245, filed on Oct. 30, 2020, which claims the benefit of, and priority to, U.S. Provisional Patent Application No. 62/928,911, filed on Oct. 31, 2019, each of which is hereby incorporated by reference herein in its entirety.

TECHNICAL FIELD

The present disclosure relates generally to systems, methods, and devices for providing smart humidification.

BACKGROUND

A conventional humidifier device—which can be stand-alone humidifier devices or humidifier modules integrated into another device or system, such as a heating, ventilation, and air conditioning system (HVAC)—simply includes a humidity sensor and adjusts humidification to reach a target humidity set point. However, simply attempting to adjust the humidity according to a set point can be insufficient to provide a benefit to a user, either because the set point is not correct for the environment of the humidifier device, the location of the humidifier device in the environment is not correct, or the humidifier device is not taking into account specific situations of the user, such as the user being sick and/or suffering from a respiratory illness or condition.

Accordingly, needs exists for methods, systems, and devices that provide smart humidification that alleviate or correct the above issues.

SUMMARY

According to one implementation of the present disclosure, a method is disclosed for providing a personalized humidification level. Aspects of the method include receiving, from a first sensor, one or more environmental parameters regarding conditions of an environment. Aspects of the method also include receiving, from a second sensor, one or more physiological parameters associated with a user within the environment. Aspects of the method also include determining an action associated with a desired change in humidity within the environment based, at least in part, on the one or more environmental parameters and the one or more physiological parameters. Aspects of the method also include causing, at least in part, a performance of the action associated with the change in the humidity in the environment based, at least in part, on moisture outputted by a humidifier module. The humidifier module is configured to output moisture for changing the humidity in the environment.

Additional aspects of the implementation include the action being a location change of the humidifier module within the environment. Additional aspects of the implementation include the action indicating to the user to a recommendation on where to move the humidifier module based on the location change. Additional aspects of the implementation include the method including processing the one or more environmental parameters and the one or more physiological parameters to determine a position of the humidifier module relative to the user within the environment. The location change is based on the position of the humidifier module relative to the user. Additional aspects of the implementation include the one or more environmental parameters including audio information associated with the environment. Additional aspects of the implementation include the one or more physiological parameters including audio information associated with the user. Additional aspects of the implementation include the environment including one or more other users. For this aspect, the method includes determining that the user is a more vulnerable person relative to the one or more other users within the environment. Additional aspects of the implementation include the user being the more vulnerable person based, at least in part, on having an asthma attack, a coughing fit, chronic obstructive pulmonary disease, or another respiratory condition. Additional aspects of the implementation include receiving one or more meteorological parameters indicative of conditions outside of the environment of the user, and determining one or more optimal conditions for the humidifier module based on the one or more environmental parameters and the one or more meteorological parameters. The determined action being associated with a desired change in the humidity is based, at least in part, on the optimal conditions. Additional aspects of the implementation include the one or more physiological parameters including heart rate, body temperature, activity level, hydration level, one or more sounds generated by the user, or a combination thereof. Additional aspects of the implementation include an electronic device associated with the user. The method then includes receiving one or more other physiological parameters from the electronic device. The determination of the action associated with a desired change in the humidity within the environment is based on one or more environmental parameters, physiological parameters, other physiological parameters or a combination thereof. Additional aspects of the implementation include the one or more other physiological parameters from the electronic device being age, gender, body mass index, one or more medical conditions, one or more preexisting conditions, self-reported current of previous comfort level, or a combination thereof. Additional aspects of the implementation include one or more of the first sensor and the second sensor are integrated into the electronic device. Additional aspects of the implementation include the one or more sounds correlating to breathing rate, breathing depth, breathing quality, coughing, wheezing, whistling, snoring, or a combination thereof. Additional aspects of the implementation include the one or more environmental parameters including temperature, barometric pressure, air quality, wind chill, a location or a combination thereof. Additional aspects of the implementation include the step of identifying an effect of a change in the humidity based on the one or more physiological parameters of the user. Additional aspects of the implementation include the humidifier module being integrated into a respiratory therapy system. Additional aspects of the implementation include the respiratory therapy system being a positive airway pressure device. Additional aspects of the implementation include the humidifier module being integrated into a heating, ventilation and/or air condition system. Additional aspects of the implementation include the second sensor being one of: a passive acoustic sensor, an active acoustic sensor, a passive radio frequency sensor, an active radio frequency sensor, a passive infrared sensor, an active infrared sensor, an optical sensor, or a video sensor. Additional aspects of the implementation include the first sensor, the second sensor, or a combination thereof being integrated in a watch, a ring, a bracelet, a necklace, a patch, clothing, a mattress, a car seat, or a combination thereof. Additional aspects of the implementation include the system being a stand-alone device.

According to another implementation of the present disclosure, a method for providing smart humidification includes controlling a humidifier module configured to output moisture for changing humidity in an environment of the humidifier module at a first set of conditions. The method further includes monitoring for a change in the humidity in the environment in response to the first set of conditions. The method further includes causing, at least in part, an alert to relocate the humidifier module within the environment based, at least in part, on the monitoring for the change in the humidity.

Additional aspects of the implementation include the monitoring for the change in the humidity including receiving information from one or more sensors indicative of the change in the humidity. Additional aspects of the implementation include the step of receiving location information from at least one of the one or more sensors indicative of a location of the humidifier module relative to the one or more sensors or to a user. Additional aspects of the implementation include the step of determining a new location where to relocate the humidifier module in the environment relative to the one or more sensors or the user based, at least in part, on the location information. Additional aspects of the implementation include the step of receiving sound information from one or more sound sensors configured to detect sound within the environment. The implementation further includes the step of processing the sound information to determine a location of the humidifier module within the environment. The implementation further includes the step of determining a new location where to relocate the humidifier module based, at least in part, on the sound information. Additional aspects of the implementation include the sound information including information indicative of a location of a user within the environment. Additional aspects of the implementation include the new location being relative to the user.

According to another implementation of the present disclosure, a method for optimizing a personalized humidification includes receiving, from one or more sensors, a first set of one or more physiological parameters associated with a user within an environment. The method further includes adjusting one or more operating conditions of a humidifier module configured to output moisture to effect a change in the humidity of the environment. The method further includes receiving, from the one or more sensors, a second set of one or more physiological parameters associated with the user the in the environment. The method further includes determining an effect on the user in response to the change in the humidity based, at least in part, on a comparison of the first and second set of one or more physiological parameters.

Additional aspects of the implementation include the one or more of the first set or the second set of physiological parameters including a respiratory parameter. Additional aspects of the implementation include the change in the humidity of the environment being within a predefined range. Additional aspects of the implementation include the step of causing, at least in part, a change in one or more operating conditions of an air purifier configured to remove particulates from air within the environment, based, at least in part, on the first set of one or more physiological parameters, the second set of one or more physiological parameters, the effect on the user in response to the change in the humidity, or a combination thereof.

According to another implementation of the present disclosure, a method includes the step of receiving from a respiratory therapy system information on operation of a humidifier unit, the respiratory therapy system configured to provide, via a user interface, an airflow to airways of the user for respiratory treatment, the respiratory therapy system comprising the humidifier unit, the humidifier unit configured to output moisture into the airflow. The method further includes the step of receiving, from a first sensor, one or more environmental parameters regarding conditions of an environment of the respiratory therapy system. The method further includes the step of adjusting one or more operation parameters of the humidifier unit or a humidifier module based, at least in part, on the information on operation of the humidifier unit and the one or more environmental parameters, the humidifier module configured to output moisture for changing humidity in an environment of the humidifier unit.

Additional aspects of the implementation include the step of receiving, from a second sensor, one or more physiological parameters associated with a user within the environment of the device. The adjustment of the one or more operation parameters is based, at least in part, on the one or more physiological parameters. Additional aspects of the implementation include the one or more physiological parameters being associated with a leak at the user interface, and the adjustment of the one or more operation parameters being based on minimizing drying of the user's airway based on the leak. Additional aspects of the implementation include the humidifier unit being a waterless humidifier unit.

According to another implementation of the present disclosure, a method for providing personalized environmental conditions is disclosed. The method includes the step of receiving, from a first sensor, one or more environmental parameters regarding the conditions of an environment. The method includes the step of receiving, from a second sensor, one or more physiological parameters associated with a user within the environment. The method includes the step of determining an action associated with a desired change in the conditions within the environment based, at least in part, on the one or more environmental parameters and the one or more physiological parameters. The method includes the step of causing, at least in part, a performance of the action associated with the change in the conditions in the environment based, at least in part, on operation of the environment modification module. The environment modification module is configured to modify conditions of an environment of the system.

Additional aspects of the implementation include the action being indicating to the user to move the environment modification module. Additional aspects of the implementation include the step of processing the one or more environmental parameters and the one or more physiological parameters to determine a position of the environment modification module relative to the user within the environment. The desired location change is at least partially based on a current position of the environment modification module relative to the user. Additional aspects of the implementation include the step of receiving one or more meteorological parameters indicative of conditions outside of the environment of the user. The method further includes the step of determining one or more optimal conditions for the environment modification module based on the one or more environmental parameters and the one or more meteorological parameters. The action includes changing an operational output based, at least in part, on the operation of the environment modification module, wherein the operational output is at least one of humidification, dehumidification, heating, cooling, and air quality modification. Additional aspects of the implementation include the step of receiving one or more other physiological parameters from an electronic device associated with the user. The determining the action associated with a desired change in the conditions within the environment is based on one or more environmental parameters, physiological parameters, other physiological parameters or a combination thereof.

According to another implementation of the present disclosure, a system for providing a personalized humidification level is disclosed. The system includes a control system including one or more processors, and a memory having stored thereon machine readable instructions. The control system is coupled to the memory, and any one or more of the above implementations are performed when the machine executable instructions in the memory are executed by at least one of the one or more processors of the control system.

According to another implementation of the present disclosure, a system providing a personalized humidification level is disclosed. The system includes a control system configured to implement the method of any one or more of the above implementations.

According to another implementation of the present disclosure, a computer program product is disclosed that includes instructions that, when executed by a computer, cause the computer to carry out the method of any one or more of the above implementations. The computer program product can be a non-transitory computer readable medium.

According to one implementation of the present disclosure, a system is configured to provide a personalized humidification level. The system includes a humidifier module configured to output moisture for changing humidity in an environment of the system. The system further includes memory storing machine readable instructions and a control system with one or more processors. The one or more processors are configured to execute the machine readable instructions to receive, from a first sensor, one or more environmental parameters regarding conditions of the environment. The one or more processors are configured further to execute the machine readable instructions to receive, from a second sensor, one or more physiological parameters associated with a user within the environment. The one or more processors are configured further to execute the machine readable instructions to determine an action associated with a desired change in the humidity within the environment based, at least in part, on the one or more environmental parameters and the one or more physiological parameters. The one or more processors are configured further to execute the machine readable instructions to cause, at least in part, a performance of the action associated with the change in the humidity in the environment based, at least in part, on moisture outputted by the humidifier module.

Additional aspects of the implementation include the action being a location change of the humidifier module within the environment. Additional aspects of the implementation include the action being indicating to the user to move the humidifier module based on the location change caused by a recommendation outputted by the one or more processors. Additional aspects of the implementation include the one or more processors being configured to execute the machine readable instructions to process the one or more environmental parameters and the one or more physiological parameters to determine a position of the humidifier module relative to the user within the environment. The location change is based on the position of the humidifier module relative to the user. Additional aspects of the implementation include the one or more environmental parameters and the one or more physiological parameters including audio information associated with the user and the environment. Additional aspects of the implementation include the environment including one or more other users. The one or more processors are configured to execute the machine readable instructions to determine that the user is a more vulnerable person relative to the one or more other users within the environment. Additional aspects of the implementation include the user being the more vulnerable person based, at least in part, on having an asthma attack, a coughing fit, chronic obstructive pulmonary disease, or another respiratory condition. Additional aspects of the implementation include the one or more processors being configured to execute the machine readable instructions to receive one or more meteorological parameters indicative of conditions outside of the environment of the user; and determine one or more optimal conditions for the humidifier module based on the one or more environmental parameters and the one or more meteorological parameters. The action includes changing the humidification output based, at least in part, on the optimal conditions. Additional aspects of the implementation include the one or more physiological parameters including heart rate, body temperature, activity level, hydration level, one or more sounds generated by the user, or a combination thereof. Additional aspects of the implementation include the system including an electronic device associated with the user. The one or more processors are configured to execute the machine readable instructions to receive one or more physiological parameters from the electronic device. Additional aspects of the implementation include the one or more physiological parameters from the electronic device including age, gender, body mass index, one or more medical conditions, one or more preexisting conditions, self-reported quality of sleep, self-reported current of previous comfort level, or a combination thereof. Additional aspects of the implementation include one or more of the first sensor and the second sensor being integrated into the electronic device. Additional aspects of the implementation include the one or more sounds correlating to breathing rate, breathing depth, breathing quality, coughing, wheezing, whistling, snoring, or a combination thereof. Additional aspects of the implementation include the one or more environmental parameters including temperature, barometric pressure, air quality, wind chill, a location or a combination thereof. Additional aspects of the implementation include the one or more processors being configured to execute the machine readable instructions to identify an effect of a change in the humidity based on the one or more physiological parameters of the user. Additional aspects of the implementation include the humidifier module being integrated into a respiratory therapy system. Additional aspects of the implementation include the respiratory therapy system being a continuous positive airway pressure device. Additional aspects of the implementation include the humidifier module being integrated into a HVAC system. Additional aspects of the implementation include the second sensor being one of: a passive acoustic sensor, an active acoustic sensor, a passive radio frequency sensor, an active radio frequency sensor, a passive infrared sensor, an active infrared sensor, an optical sensor, or a video sensor. Additional aspects of the implementation include the first sensor, the second sensor, or a combination thereof is integrated in a watch, a ring, a bracelet, a necklace, a patch, clothing, a mattress, a car seat, or a combination thereof. Additional aspects of the implementation include the system being a stand-alone device.

According to some implementations of the present disclosure, a system is disclosed that is configured to provide smart humidification. The system includes a humidifier module configured to output moisture for changing humidity in an environment of the humidifier module. The system also includes memory storing machine readable instructions; and a control system with one or more processors. The one or more processors are configured to execute the machine readable instructions to control the humidifier module at a first set of conditions. The one or more processors are configured further to execute the machine readable instructions to monitor for a change in the humidity in the environment in response to the first set of conditions. The one or more processors are configured further to execute the machine readable instructions cause, at least in part, an alert to relocate the humidifier module within the environment based, at least in part, on the monitoring for the change in the humidity.

Additional aspects of the implementation include one or more sensors being located within the environment. In which case, the monitoring for the change in the humidity includes receiving information from at least one of the one or more sensors indicative of the change in the humidity. Additional aspects of the implementation include the one or more processors being configured to execute the machine readable instructions to receive location information from at least one of the one or more sensors indicative of a location of the humidifier module relative to the one or more sensors or to a user. Additional aspects of the implementation include the one or more processors being configured to execute the machine readable instructions to determine a new location where to relocate the humidifier module in the environment relative to the one or more sensors or the user based, at least in part, on the location information. Additional aspects of the implementation include the one or more processors being configured to execute the machine readable instructions to receive sound information from one or more sound sensors configured to detect sound within the environment; process the sound information to determine a location of the humidifier module within the environment; and determine a new location where to relocate the humidifier module based, at least in part, on the sound information. Additional aspects of the implementation include the sound information including information indicative of a location of a user within the environment. Additional aspects of the implementation include the new location being relative to the user.

According to one implementation of the present disclosure, a system is configured to optimize a personalized humidification level. The system includes a humidifier module configured to output moisture for changing humidity in an environment of the device. The system further includes memory storing machine readable instructions and a control system with one or more processors. The one or more processors are configured to execute the machine readable instructions to receive, from one or more sensors, a first set of one or more physiological parameters associated with a user within the environment. The one or more processors are configured further to execute the machine readable instructions to adjust one or more operating conditions of the humidifier module to effect a change in the humidity of the environment. The one or more processors are configured further to execute the machine readable instructions to receive, from the one or more sensors, a second set of one or more physiological parameters associated with the user the in the environment. The one or more processors are configured further to execute the machine readable instructions to determine an effect on the user in response to the change in the humidity based, at least in part, on a comparison of the first and second set of one or more physiological parameters.

Additional aspects of the implementation include the one or more physiological parameters being a respiratory parameter. Additional aspects of the implementation include the change in the humidity of the environment being within a predefined range. Additional aspects of the implementation include the system including an air purifier configured to remove particulates from air within the environment. In which case, the one or more processors are configured to execute the machine readable instructions to cause, at least in part, a change in one or more operating conditions of the air purifier based, at least in part, on the first set of one or more physiological parameters, the second set of one or more physiological parameters, the effect on the user in response to the change in the humidity, or a combination thereof.

According to one implementation of the present disclosure, a humidifier device is configured to operate in conjunction with a respiratory treatment system configured to provide an airflow to a user for respiratory treatment, the respiratory treatment system comprising a humidifier unit configured to output moisture into the airflow. The humidifier device includes a humidifier module configured to output moisture for changing humidity in an environment of the humidifier unit. The humidifier device further includes memory storing machine readable instructions and a control system with one or more processors. The one or more processors are configured to execute the machine readable instructions to receive from respiratory therapy system information on operation of the humidifier unit. The one or more processors are configured further to execute the machine readable instructions to receive, from a first sensor, one or more environmental parameters regarding conditions of the environment of the respiratory therapy system. The one or more processors are configured further to execute the machine readable instructions to adjust one or more operation parameters of the humidifier unit or the humidifier device, based, at least in part, on the information on operation of the humidifier unit and the one or more environmental parameters.

Additional aspects of the implementation include the one or more processors being configured to execute the machine readable instructions to receive, from a second sensor, one or more physiological parameters associated with a user within the environment of the device. The adjustment of the one or more operation parameters can be based, at least in part, on the one or more physiological parameters. Additional aspects of the implementation include the one or more physiological parameters being associated with leak at the user interface, and the adjustment of the one or more operation parameters is based on minimizing drying of the user's airway based on the leak. Additional aspects of the implementation include the humidifier unit being a waterless humidifier unit.

According to one implementation of the present disclosure, a system is provided that is configured to provide a personalized environmental conditions. The system includes an environment modification module configured to modify conditions of an environment of the system. The system further includes memory storing machine readable instructions and a control system with one or more processors. The one or more processors are configured to execute the machine readable instructions to receive, from a first sensor, one or more environmental parameters regarding the conditions of the environment. The one or more processors are configured further to execute the machine readable instructions to receive, from a second sensor, one or more physiological parameters associated with a user within the environment. The one or more processors are configured further to execute the machine readable instructions to determine an action associated with a desired change in the conditions within the environment based, at least in part, on the one or more environmental parameters and the one or more physiological parameters. The one or more processors are configured further to execute the machine readable instructions to cause, at least in part, a performance of the action associated with the change in the conditions in the environment based, at least in part, on operation of the environment modification module.

Additional aspects of the implementation include the action being indicating to the user to move the environment modification module based on the location change caused by a recommendation outputted by the one or more processors. Additional aspects of the implementation include the one or more processors are configured to execute the machine readable instructions to process the one or more environmental parameters and the one or more physiological parameters to determine a position of the environment modification module relative to the user within the environment. The desired location change can be based, at least in part, on a current position of the environment modification module relative to the user. Additional aspects of the implementation include the one or more processors being configured to execute the machine readable instructions to receive one or more meteorological parameters indicative of conditions outside of the environment of the user, and determine one or more optimal conditions for the environment modification module based on the one or more environmental parameters and the one or more meteorological parameters. The action can be changing an operational output based, at least in part, on the operation of the environment modification module. The operational output can be at least one of humidification, dehumidification, heating, cooling, and air quality modification. Additional aspects of the implementation include an electronic device associated with the user. The one or more processors can be configured to execute the machine readable instructions to receive one or more other physiological parameters from the electronic device. The determining of the action associated with a desired change in the conditions within the environment can be based on one or more environmental parameters, physiological parameters, other physiological parameters or a combination thereof.

The above summary is not intended to represent each embodiment or every aspect of the present invention. Additional features and benefits of the present invention are apparent from the detailed description and figures set forth below.

Figure 1:
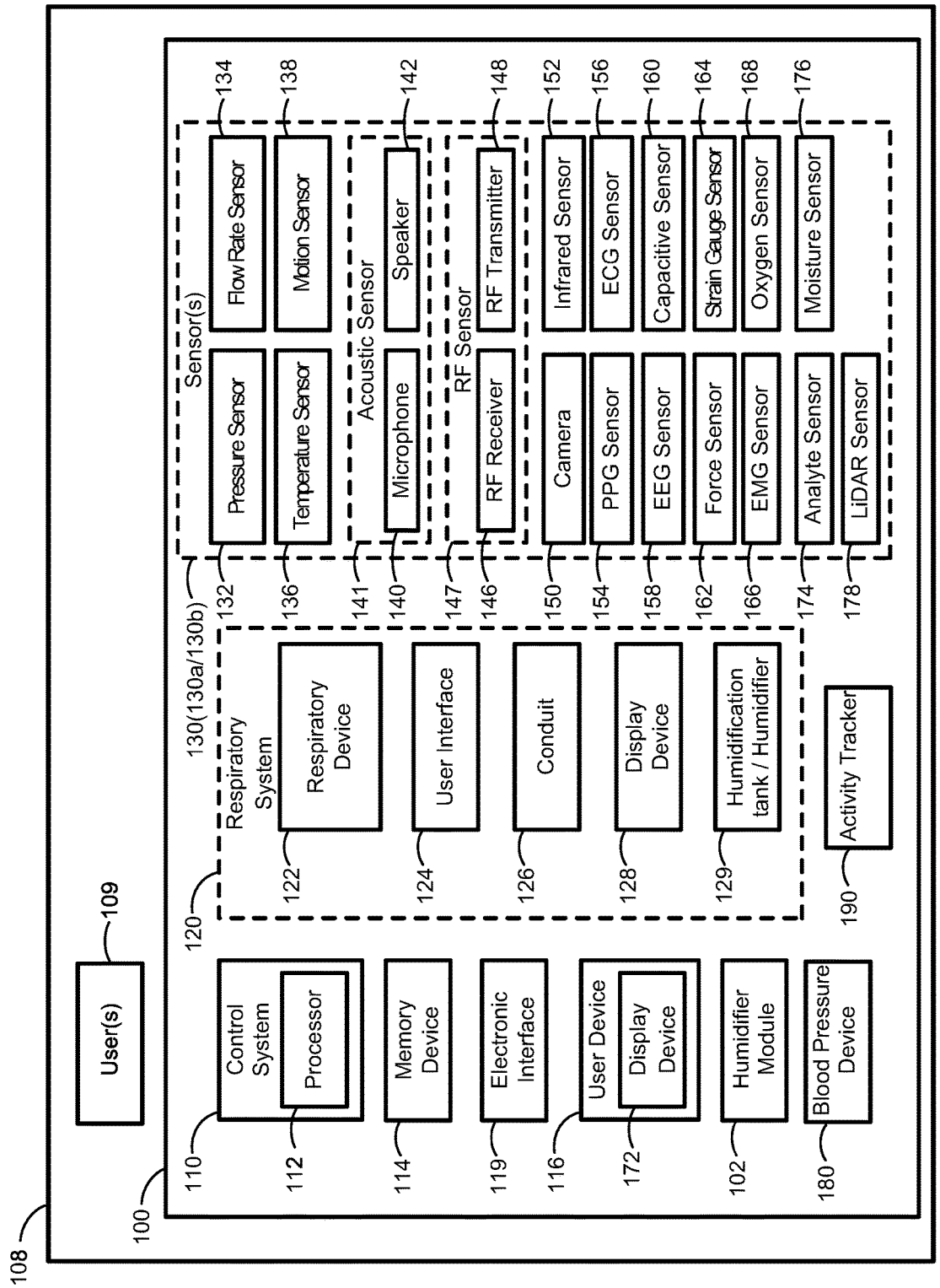
FIG. 1 is a functional block diagram of a system for providing personalized humidification, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

To simplify discussion, the singular form will be used for all components disclosed herein, when appropriate, but the use of the singular does not limit the discussion to only one of each component.

The methods, systems, and devices of the present disclosure provide for personalized humidification based on a user's (or users') personal requirements. For an example, for the general population, dry air (relative humidity (RH) less than 40%) can cause issues that are triggered at different levels. One person may suffer no ill effects at 30% RH (e.g., perhaps just having dry skin), whereas another person may have an increased probability of experiencing a respiratory exacerbation (particularly if combined with low temperature) due to the drying of nasal passages and worsening of airway inflammation. Accordingly, the personalized humidification of the present methods, systems, and devices can alleviate or prevent the respiratory exacerbation. The personalized humidification can include, for example, adapting humidification levels to best combat symptoms of discomfort or a breathing issue, such as breathing issues related to allergies, asthma, Chronic Obstructive Pulmonary Disease (COPD), sleep-disordered breathing (SDB), etc. The methods, systems, and devices of the present disclosure can provide automated, personalized control over humidity, with the end goal being better breathing. Better breathing can be associated with improved comfort and reduced frequency or severity of illness or condition, as examples.

The methods, systems, and devices of the present disclosure can measure user's physiological parameters and control the humidity of the user's environment. In one or more implementations, the physiological parameters can be detected using room or area or building management sensors and/or systems and/or inputted by the user, such as through an electronic device.

In one or more implementations, the methods, systems, and devices can learn changes in humidity based on the physiological and/or environmental parameters that relate to the quality of the breathing of a user. The physiological parameters can be based on audible sounds, detected motion due to breathing, etc. In one or more implementations, breathing quality can be based on breathing rate, breathing depth; alone or in comparison to population normative values based on age, gender, location (relating to air quality, temperature, weather, climate, etc.) or a personalized target "good" breathing curve and parameters. The physiological parameters can also be heart rate, body temperature, body mass index (BMI), activity levels, hydration levels, medical conditions, pre-existing conditions, ongoing therapy, etc.

In one or more implementations, the breathing quality can be determined by the detection of inspiration, pause, and expiration, and estimating breathing rate and other metrics including depth of breathing (e.g., to detect shallow, panting breathing, or normal breathing). This can be achieved by a multitude of contact or non-contact sensors, as discussed below. Other markers, such as coughing, wheezing, whistling, snoring when asleep, etc. can be detected.

In one or more implementations, personalized humidification can be provided to a user to adjust humidity in the environment of the user, such as by adjusting operation of a humidifier module, to achieve a desired physiological state of the user. For example, the user may have a cold or other condition that affects the respiration of the user. The desired physiological state can relate to, for example, the comfort level of the user's respiration. The humidity in the environment can be controlled through an action of a humidifier module to achieve a desired humidity level that improves, for example, the breathing of the user, reduces coughing of the user, or improves some other respiratory related condition. Aspects of the present disclosure allow this process to be automated such that the user does not need to know what humidity level will improve the physiological state. Rather, the process can independently detect conditions of the user that relate to physiological states and then control the humidity within an environment to improve the physiological state.

Other physiological states can be improved by the methods of the present disclosure. For example, in one or more implementations, the physiological state of the user can be a desired sleep state (e.g., awake or sleep) or a desired sleep stage (e.g., N1, N2, REM, etc.), which are both further discussed below. The humidity within an environment, such as the ambient humidity in the air, and/or humidity generated by the humidifier of a respiratory therapy system, can be controlled to achieve desired sleep states and/or sleep stages throughout one or more sleep sessions. Physiological parameters of a user can be detected that are associated with detecting the sleep state and/or sleep stage of the user. Implementations of the present disclosure can then adjust one or more operating conditions of, for example, a humidifier module and/or a humidifier of a respiratory therapy device to effect a change in the humidity of the environment, which in turn achieves a desired sleep state (e.g., asleep) and/or a desired sleep stage (e.g., REM or N3) or a desired pattern of sleep stages through a portion of a sleep session or the entire sleep session. The effect on the sleep state and/or sleep stage can be tied to a user having a specific physiological state, such as having a cold, or be independent of the user having a specific physiological state, such as a normal, healthy user simply obtaining a better night's rest.

In one or more implementations, the methods, systems, and devices can include making recommendations based on the location of a humidifier module or humidifier in an environment, as well as adapting the humidity target range. For example, there may be the correct target humidity level but perhaps not the correct target location of the humidifier module or humidifier device in an environment, such as a room. The location of the humidifier module or humidifier device can be sensed based on, for example, the same sound detection used to detect audible sounds made by a user or the respiration of the user, that relate to changes in the humidity.

Referring to FIG. 1, a system 100 is illustrated that provides a personalized humidification level, according to some implementations of the present disclosure. The system 100 includes a humidifier module 102, a control system 110, a memory device 114, and an electronic interface 119. The system 100 further includes one or more sensors 130. The system 100 is located in an environment 108. Within the environment 108 are one or more users 109.

The humidifier module 102 can be a room or area-specific humidifier module, such as an evaporator that uses a filter wick and fan, an impeller humidifier that uses a rotating disc, a steam vaporizer that heats water to produce vapor, an ultrasonic humidifier that uses vibrations to create the vapor, or a central humidifier integrated into a home or commercial heating, ventilation and/or air conditioning unit (HVAC unit).

In one or more implementations, the humidifier module 102 can be included in a respiratory therapy system 120, such as a continuous positive airway pressure (CPAP) device, within the system 100. Alternatively, or in addition, the humidifier module 102 can be separate from the respiratory therapy system 120. Alternatively, the humidifier module 102 can be within a heating, ventilation, and/or air conditioning system, a local humidifier, or a separate device that affects humidity. Thus, the humidifier module 102 can be, or be within, a stand-alone device. The stand-device, also referred to as a humidifier device, can also include one or more of the control system 110, the memory device 114, the one or more sensors 130 (e.g., the first sensor and/or the second sensor, discussed below), and the electronic device and/or user device 116 (discussed below). Such a stand-alone device can be configured for operating in conjunction with the respiratory therapy system 120 used by the user 109, particularly for if the respiratory therapy system 120 does have humidification capabilities.

In cases of higher humidity (e.g., over 60% RH), a dehumidifier function may be employed to reduce the possibility of mold buildup, dust mites and so forth in the environment 108 (such as a room) that could potentially worsen respiratory conditions if not managed. In one or more implementations, the humidifier module 102 can also include a unit (not shown) that performs dehumidification. Such a dehumidification unit can include a fan that cools a metal plate and captures condensed moisture from the air; a desiccant that absorbs water from the air using a desiccant on a wheel, which then warms to drive off moisture to be collected;

and/or central dehumidifiers integrated into home or commercial heating and ventilation systems.

Although disclosed throughout as a humidifier module 102, in one or more implementations, the humidifier module 102 can be any type of environment modification device or module within a device. For example, the humidifier module 102 can instead be a humidifier; a de-humidifier; a heater, with or without a humidifier; an air conditioning unit, with or without a humidifier; an air purifier; etc. Thus, the humidifier module 102 can instead be any unit that can modify environmental parameters of the environment. Further, any discussion regarding the change or control of humidity can instead be a change in the operating conditions of the environment modification device. The change in the operating conditions can be based on a change in output of at least one of humidification, dehumidification, heating, cooling, air quality modification, etc.

The environment 108 can be any closed, or partially closed, area, such as a room (e.g., room in a house, in an office, in a hotel, etc.), a building, a vehicle (e.g., a car, a truck, a train car, a plane cabin, etc.), etc. For example, the environment 108 can be an entire house, condo, etc., or a specific room (e.g., in the case where an HVAC covers many areas).

The environment 108 is surrounded by an outside area 118. The outside area is generally considered as not having the humidity controlled or affected by the humidifier module 102. Thus, for example, the outside area 118 can be outside of a room or outside of a house.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 116, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The control system 110 generally controls the various components of the system 100 and/or analyzes data obtained and/or generated by the components of the system 100. The control system 110 executes machine readable instructions that are stored in the memory device 114 or a different memory device. The control system 110 can implement one or more engines of the system 100. An engine is a combination of hardware and software configured to perform specific functionality. The one or more processors of the control system 110 can be general or special purpose processors and/or microprocessors.

While the control system 110 is described and depicted in FIG. 1 as being a separate and distinct component of the system 100, in some implementations, the control system 110 is integrated in and/or directly coupled to the humidifier module 102. For example, the control system 110 can be coupled to and/or positioned within a housing of the humidifier module 102 or any combination thereof.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While the system 100 is shown as including a single memory device 114, it is contemplated that the system 100 can include any suitable number of memory devices (e.g., one memory device, two memory devices, five memory devices, ten memory devices, etc.). The memory device 114 can be any suitable computer readable storage device or media, such as, for example, a random or serial access memory device, a hard drive, a solid state drive, a flash memory device, etc. The memory device 114 can be coupled to and/or positioned within a housing of the humidifier module 102 and/or positioned within a housing of any one or more of the sensors 130. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 116 and/or the humidifier module 102. In other implementations, the electronic interface 119 is coupled to or integrated (e.g., in a housing) with the control system 110 and/or the memory device 114.

As noted above, in some implementations, the system 100 optionally includes a respiratory system 120 (also referred to as a respiratory therapy system). The respiratory system 120 can include a device 122 (also referred to as a respiratory pressure therapy device), a user interface 124, a conduit 126 (also referred to as a tube or an air circuit), a display device 128, a humidification tank and/or a humidifier 129, or any combination thereof. In some implementations, the control system 110, the memory device 114, the display device 128, one or more of the sensors 130, and the humidifier 129 are part of the respiratory device 122.

Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory device 122.

The user interface 124 engages a portion of a user 109's face and delivers pressurized air from the respiratory device 122 to the user 109's airway to aid in preventing the airway from narrowing and/or collapsing during sleep. This may also increase the user 109's oxygen intake during sleep. Depending upon the therapy to be applied, the user interface 124 may form a seal, for example, with a region or portion of the user 109's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
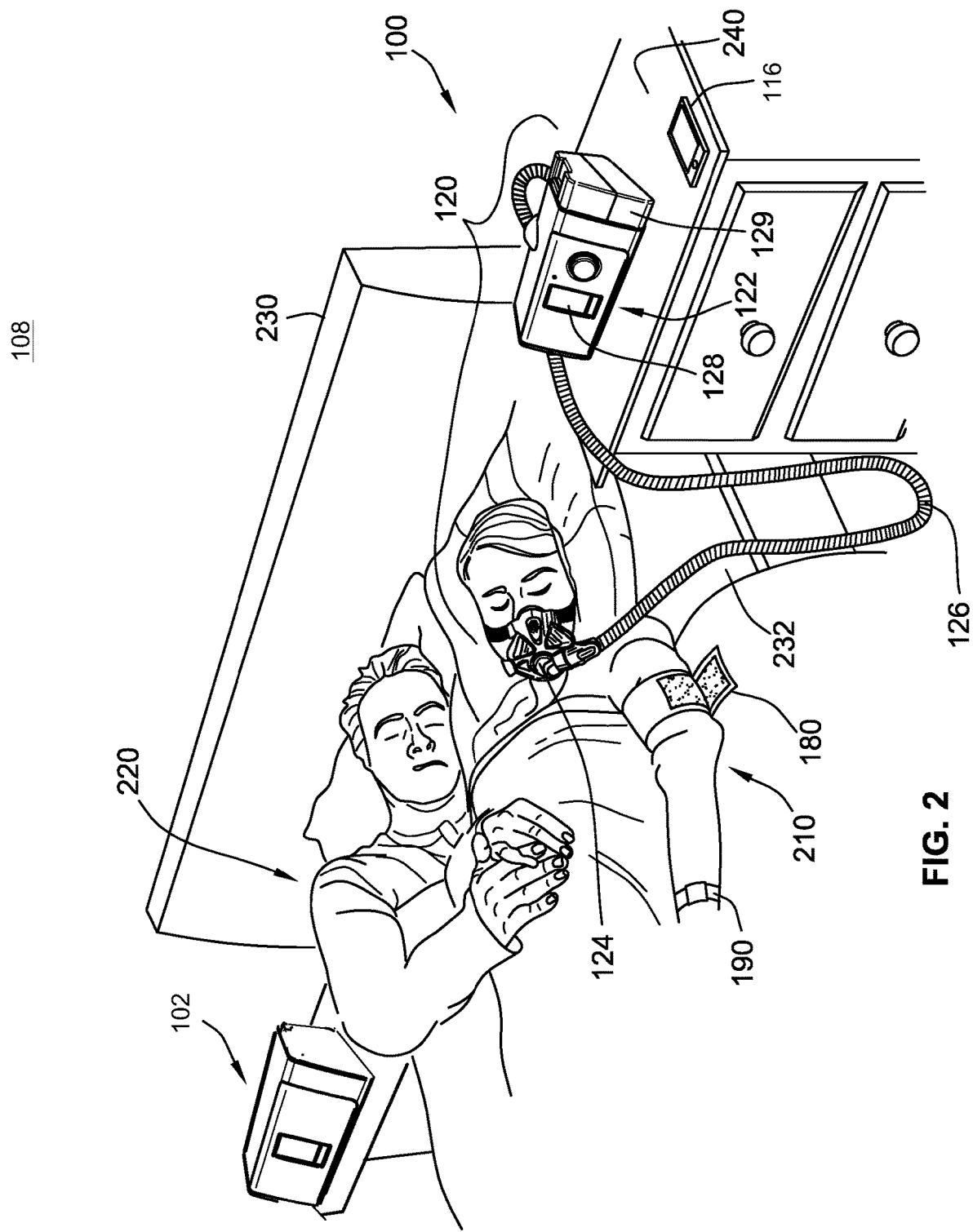
FIG. 2 is a perspective view of an environment of the system of FIG. 1, with a user of the system, and a bed partner of the user, according to some implementations of the present disclosure.

As shown in FIG. 2, in some implementations, the user interface 124 is or includes a facial mask that covers the nose and mouth of the user. Alternatively, the user interface 124 is or includes a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a portion of the user interface 124 on a desired location of the user (e.g., the face), and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the user's teeth, a mandibular repositioning device, etc.).

The conduit 126 allows the flow of air between two components of a respiratory system 120, such as the respiratory device 122 and the user interface 124. In some implementations, there can be separate limbs of the conduit 126 for inhalation and exhalation. In other implementations, a single limb conduit is used for both inhalation and exhalation.

One or more of the respiratory device 122, the user interface 124, the conduit 126, the display device 128, and the humidification tank and/or humidifier 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score or a therapy score (also referred to as a myAir™ score), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank and/or humidifier 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. In other implementations, the respiratory device 122 or the conduit 126 can include a waterless humidifier 129 (e.g., humidifier without a water tank). The waterless humidifier 129 can incorporate sensors that interface with other sensor positioned elsewhere in system 100.

The respiratory system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based at least in part on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 (e.g., one of user(s) 109 of FIG. 1) of the respiratory system 120 and a bed partner 220 (e.g., one of user(s) 109 of FIG. 1) are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, as discussed in greater detail below, the sensors 130 can include a first sensor 130a and a second sensor 130b. The first sensor 130a can be any one or more of the sensors 130 that can detect environmental parameters regarding conditions of the environment 108. The environmental parameters can be audio-based, light-based, touch-based, motion-based, etc. In one or more implementations, the first sensor 130a can be a temperature and/or a humidity sensor. Humidity sensors can include a capacitive sensor (humidity-dependent condenser), a resistive sensor (measure the electrical change in conductive polymers/treated substrates), and a thermal conductivity sensor (difference between thermal conductivity of dry and of moist air). In one or more implementations, the first sensor 130a can be a standalone sensor either provided with the system 100, built into the environment 108 (e.g., walls/ceiling of a smart building), or integrated into another electronic device in the environment 108, such as a smart speaker or a television with a microphone to detect the location of the user 109 and the humidifier module 102.

The second sensor 130b can be any one or more of the sensors 130 that can detect one or more physiological parameters of the user(s) 109. For example, the second sensor 130b can be an acoustic sensor, a resistive sensor, a capacitive sensor, a piezoelectric sensor, a MEMS accelerometer sensor, an optical sensor, a pressure sensor, a temperature sensor, a charged thin film sensor or other type of sensor. The physiological parameters can be, for example, heart rate, body temperature, activity level, hydration level, one or more sounds generated by the user, or a combination thereof, or any other physiological parameter.

In one or more implementations, the second sensor 130b can include and provide information that is inputted by the user 109 that corresponds to the one or more physiological parameters. For example, the user 109 can input information into the second sensor 130b regarding their comfort level, such as their comfort level with respect to respiration, including subjective information related to breathing. The self-reported information inputted into the second sensor 130b could also include data on a medical condition severity/progression.

The second sensor 130b can also be a standalone sensor provided with the system 100, built into the environment 108 (e.g., walls/ceiling of a smart building) or integrated into another electronic device in the environment 108. Thus the second sensor 130b can be one or more of a passive acoustic sensor, an active acoustic sensor, a passive radio frequency sensor, an active radio frequency sensor, a passive infrared sensor, an active infrared sensor, an optical sensor, or a video sensor. For example, the second sensor 130b can be one or more passive audio sensor listening for sounds of breathing, one or more active acoustic sensors that process a reflected audio and/or ultrasonic signal from an object, one or more passive radio frequency sensors that process reflections in an electromagnetic signal (e.g., Wi-Fi, cellular, satellite, digital TV or other signals), one or more active radio frequency sensors such as (e.g., RF RADAR such as CW, pulsed CW, FSKCW, PSKCW, FMCW, UWB, RF imaging, etc. using time of flight, phase change, Doppler shift, etc.), one or more passive infrared and/or active infrared processing an echo, one or more optical sensors such as video photoplethysmograpy (PPG). An active and/or passive acoustic sensor could for example be in a smartphone, tablet, smart-speaker, car stereo, radio, TV etc. The second sensor 130b can also, or in the alternative, be one or more contact sensors that can perform the above or alternative sensing functionalities/modalities.

In one or more implementations, the first sensor 130a, the second sensor 130b, or both can be separate or integrated into a wearable device, such as a watch, a ring, an earring, an earpiece, a bracelet, a necklace, a patch, clothing, a mattress, a car seat, or a combination thereof, as further discussed below.

In more detail, the one or more sensors 130 (e.g., and first sensor 130a and second sensor 130b) of the system 100 can include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LidAR sensor 178, more generally, the one or more sensors 130 can include any combination and any number of each of the sensors described and/or shown herein, including one or more of the sensors being omitted.

The one or more sensors 130 can be used to generate, for example physiological data, audio data, or both. Physiological data generated by one or more of the sensors 130 can be used by the control system 110 to determine a sleep-wake signal associated with a user during a sleep session and one or more sleep-related parameters. The sleep-wake signal can be indicative of one or more sleep stages, including sleep, wakefulness, relaxed wakefulness, micro-awakenings, or distinct sleep stages such as a rapid eye movement (REM) stage, a first non-REM stage (often referred to as "N1"), a second non-REM stage (often referred to as "N2"), a third non-REM stage (often referred to as "N3"), or any combination thereof.

The sleep-wake signal can also be timestamped to indicate a time that the user enters the bed, a time that the user exits the bed, a time that the user attempts to fall asleep, etc. The sleep-wake signal can be measured one or more of the sensors 130 during the sleep session at a predetermined sampling rate, such as, for example, one sample per second, one sample per 30 seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof.

Physiological data and/or audio data generated by the one or more sensors 130 can also be used to determine a respiration signal associated with a user during a sleep session. the respiration signal is generally indicative of respiration or breathing of the user during the sleep session. The respiration signal can be indicative of, for example, a respiration rate, a respiration rate variability, an inspiration amplitude, an expiration amplitude, an inspiration-expiration amplitude ratio, an inspiration-expiration duration ratio, a number of events per hour, a pattern of events, pressure settings of the respiratory device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure (e.g., pressure of the environment 108). In such implementations, the pressure sensor 132 can be coupled to or integrated in the respiratory device 122. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 109, a skin temperature of the user 109, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 109 during the sleep session, and/or detect movement of any of the components of the respiratory system 120, such as the respiratory device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user 109 and proximal to the user interface 124, and configured to detect features of the pulse shape, speed, amplitude, or volume.

The microphone 140 outputs sound data that can be stored in the memory device 114 and/or analyzed by the processor 112 of the control system 110. The audio data generated by the microphone 140 is reproducible as one or more sound(s) during a sleep session (e.g., sounds from the user 109) to determine (e.g., using the control system 110) one or more sleep-related parameters, as described in further detail herein. The audio data from the microphone 140 can also be used to identifying (e.g., using the control system 110) an event experienced by the user during the sleep session, as described in further detail herein. The microphone 140 can be coupled to or integrated in the respiratory device 122, the user interface 124, the conduit 126, or the user device 116.

The speaker 142 outputs sound waves that are audible to the user 109 of the system 100. The speaker 142 can be used, for example, as an alarm clock or to play an alert or message to the user 109 (e.g., in response to an event). In some implementations, the speaker 142 can be used to communicate the audio data generated by the microphone 140 to the user 109. The speaker 142 can be coupled to or integrated in the respiratory device 122, the user interface 124, the conduit 126, or the user device 116.

The microphone 140 and the speaker 142 can be used as separate devices. In some implementations, the microphone 140 and the speaker 142 can be combined into an acoustic sensor 141, as described in, for example, WO 2018/050913, which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 109 (or the bed partner 220 in FIG. 2). Based at least in part on the data from the microphone 140 and/or the speaker 142, the control system 110 can determine a location of the user 109 and/or one or more of the sleep-related parameters described in herein. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 109 and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 116, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 109 enters the bed 230 (FIG. 2), and to determine a time when the user 109 exits the bed 230. The camera 150 can also be used to track eye movements, pupil dilation (if one or both of the user 109's eyes are open), blink rate, or any changes during REM sleep. The camera 150 can also be used to track the position of the user 109, which can impact the duration and/or severity of apneic episodes in users 109 with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user 109 and/or movement of the user 109. The IR sensor 152 can also be used in conjunction with the camera 150 when measuring the presence, location, and/or movement of the user 109. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 109 that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 109, embedded in clothing and/or fabric that is worn by the user 109, embedded in and/or coupled to the user interface 124 and/or its associated headgear (e.g., straps, etc.), etc.

The ECG sensor 156 outputs physiological data associated with electrical activity of the heart of the user 109. In some implementations, the ECG sensor 156 includes one or more electrodes that are positioned on or around a portion of the user 109 during the sleep session. The physiological data from the ECG sensor 156 can be used, for example, to determine one or more of the sleep-related parameters described herein.

The EEG sensor 158 outputs physiological data associated with electrical activity of the brain of the user 109. In some implementations, the EEG sensor 158 includes one or more electrodes that are positioned on or around the scalp of the user 109 during the sleep session. The physiological data from the EEG sensor 158 can be used, for example, to determine a sleep stage of the user 109 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 109. The data output by the analyte sensor 174 can be stored in the memory device 114 and used by the control system 110 to determine the identity and concentration of any analytes in the user 109's breath. In some implementations, the analyte sensor 174 is positioned near a mouth of the user 109 to detect analytes in breath exhaled from the user 109's mouth. For example, when the user interface 124 is a facial mask that covers the nose and mouth of the user 109, the analyte sensor 174 can be positioned within the facial mask to monitor the user 109's mouth breathing. In other implementations, such as when the user interface 124 is a nasal mask or a nasal pillow mask, the analyte sensor 174 can be positioned near the nose of the user 109 to detect analytes in breath exhaled through the user 109's nose. In still other implementations, the analyte sensor 174 can be positioned near the user 109's mouth when the user interface 124 is a nasal mask or a nasal pillow mask. In this implementation, the analyte sensor 174 can be used to detect whether any air is inadvertently leaking from the user 109's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user 109 is breathing through their nose or mouth. For example, if the data output by an analyte sensor 174 positioned near the mouth of the user 109 or within the facial mask (in implementations where the user interface 124 is a facial mask) detects the presence of an analyte, the control system 110 can use this data as an indication that the user 109 is breathing through their mouth.

The moisture sensor 176 outputs data that can be stored in the memory device 114 and used by the control system 110. The moisture sensor 176 can be used to detect moisture in various areas surrounding the user 109 (e.g., inside the conduit 126 or the user interface 124, near the user 109's face, near the connection between the conduit 126 and the user interface 124, near the connection between the conduit 126 and the respiratory device 122, etc.). Thus, in some implementations, the moisture sensor 176 can be coupled to or integrated into the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 109, for example the air inside the user 109's bedroom. The moisture sensor 176 can also be used to track the user 109's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory device 122, the user interface 124, the conduit 126, the humidification tank/humidifier 129, the control system 110, the user device 116, or any combination thereof. For example, the acoustic sensor 141 and/or the RF sensor 147 can be integrated in and/or coupled to the user device 116. In such implementations, the user device 116 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory device 122. In some implementations, at least one of the one or more sensors 130 is not coupled to the respiratory device 122, the control system 110, or the user device 116, and is positioned generally adjacent to the user 109 during a sleep session (e.g., positioned on or in contact with a portion of the user 109, worn by the user 109, coupled to or positioned on the nightstand 240 (FIG. 2), coupled to the mattress 232 (FIG. 2), coupled to the ceiling of a (e.g., environment 108), etc.). More generally, the one or more sensors 130 can be positioned at any suitable location relative to the user 109 such that the one or more sensors 130 can generate physiological data associated with the user(s) 109 (e.g., user 210 and/or the bed partner 220 in FIG. 2) during one or more sleep sessions.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 116 (FIG. 1) includes a display device 172. The user device 116 can be, for example, a mobile device such as a smart phone, a tablet, a laptop, or the like. Alternatively, the user device 116 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 116. In some implementations, one or more user devices can be used by and/or included in the system 100.

The blood pressure device 180 is generally used to aid in generating physiological data for determining one or more blood pressure measurements associated with a user. The blood pressure device 180 can include at least one of the one or more sensors 130 to measure, for example, a systolic blood pressure component and/or a diastolic blood pressure component.

In some implementations, the blood pressure device 180 is a sphygmomanometer including an inflatable cuff that can be worn by a user and a pressure sensor (e.g., the pressure sensor 132 described herein). For example, as shown in the example of FIG. 2, the blood pressure device 180 can be worn on an upper arm of the user 210. In such implementations where the blood pressure device 180 is a sphygmomanometer, the blood pressure device 180 also includes a pump (e.g., a manually operated bulb) for inflating the cuff. In some implementations, the blood pressure device 180 is coupled to the respiratory device 122 of the respiratory system 120, which in turn delivers pressurized air to inflate the cuff. More generally, the blood pressure device 180 can be communicatively coupled with, and/or physically integrated in (e.g., within a housing), the control system 110, the memory device 114, the respiratory system 120, the user device 116, and/or the activity tracker 190.

The activity tracker 190 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 190 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 190 is a wearable device that can be worn by the user 109, such as a smartwatch, a wristband, a ring, or a patch. For example, referring to FIG. 2, the activity tracker 190 is worn on a wrist of the user 210. The activity tracker 190 can also be coupled to or integrated a garment or clothing that is worn by the user 109. Alternatively, still, the activity tracker 190 can also be coupled to or integrated in (e.g., within the same housing) the user device 116. More generally, the activity tracker 190 can be communicatively coupled with, or physically integrated in (e.g., within a housing), the control system 110, the memory device 114, the respiratory system 120, the user device 116, and/or the blood pressure device 180.

While the control system 110 and the memory device 114 are described and shown in FIG. 1 as being a separate and distinct component of the system 100, in some implementations, the control system 110 and/or the memory device 114 are integrated in the user device 116 and/or the respiratory device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in the system 100 for providing personalized humidification, according to implementations of the present disclosure. For example, a first alternative system includes the humidifier module 102, the control system 110, the memory device 114, and at least one of the one or more sensors 130. As another example, a second alternative system includes the humidifier module 102, the control system 110, the memory device 114, at least one of the one or more sensors 130, and the user device 116. As yet another example, a third alternative system includes the humidifier module 102, the control system 110, the memory device 114, the respiratory system 120, at least one of the one or more sensors 130, and the user device 116. As a further example, a fourth alternative system includes the humidifier module 102, the control system 110, the memory device 114, the respiratory system 120, at least one of the one or more sensors 130, the user device 116, and the blood pressure device 180 and/or activity tracker 190. In further examples, the microphone 140 included in the one or more sensors 130 can include the microphone 242, the feedback microphone, or both. Thus, various systems for analyzing data associated with a user's use of the respiratory system 120 can be formed using any portion or portions of the components shown and described herein for the system 100 and/or in combination with one or more other components.

As described above, one or more user devices 116 can also be within the environment. The one or more user devices 116 can be any electronic device, such as a user device, that allows a user to provide information to one or more of the humidifier module 102, the memory device 114, the control system 110, the first sensor 130*a*, or the second sensor 130*b*. For example, the one or more electronic devices 116 can be a mobile (smart) phone, a personal digital assistant, a tablet, a laptop computer, a smart television, a monitor, a terminal, a health tracker, a fitness tracker, smart speaker, smart sound bar, or any combination thereof. Although the user device 116 is illustrated as being separate from the first sensor 130*a* and the second sensor 130*b*, in one or more implementations, the first sensor 130*a*, the second sensor 130*b*, or both can be integrated into a user device 116. For example, the user device 116 can be again a smart phone or an activity tracker 190 that can detect the humidity of the environment 108 and electrocardiogram (ECG) signals and/or the respiratory signals and/or hydration level (such as using infra-red) of a user 109 wearing the fitness tracker. In one or more implementations, one or more sensors within the user device 116 can be one or more of the sensors 130*a* and 130*b*. For example, in one or more implementations, the microphone and/or speakers in a smart phone can measure respiration of the user 109, such as disclosed in International Patent Application Publication No. WO 2018/050913, which is hereby incorporated by reference herein in its entirety.

The user device 116 can provide additional physiological parameters that may not be sensed, per se, but may be provided from the user 109, say by using a user interface of the user device 116. Such additional subjective parameters may include one or more of age, gender, body mass index, one or more medical conditions, one or more pre-existing conditions, or a combination thereof. These parameters can be stored in a profile of the user 109 on the user device 116. The physiological parameters can also include subjective information from the user 109 reported through the user device 116, including reported running nose, difficulty breathing, dry skin, chest tightness, throat clearing, mucus/ sputum quantity and color, lack of energy, respiratory infections, self-reported quality of sleep, self-reported current of previous comfort level, etc.

In one or more implementations, the user device 116 can include and provide information to the control system 110 that is inputted by the user 109 that corresponds to the one or more physiological parameters, one or more environmental sensors, or a combination thereof. In such implementations, the user device 116 can be considered a sensor. Similar to discussed above, the user 109 can input information into the user device 116 regarding their comfort level, such as their comfort level with respect to respiration, including subjective information relative to breathing. The user 109 can also input certain parameters regarding the environment. The self-reported information inputted into the user device 116 could also include data on a medical condition severity/progression, such as read from an electronic health records Although only one humidifier module 102 is illustrated in the one environment 108, in one or more implementations, there can be multiple humidifier modules 102 in the environment 108, or multiple separate environments 108 with separate humidifier modules 102. In one or more implementations, there can be multiple environments 108, with each one having a similar setup as shown in FIG. 1. For example, each separate environment 108 can include its own system 100 with a humidifier module 102, control system 110, and memory device 114. The processing between the multiple control systems 110 can be centralized (either locally or remotely, such as in the cloud). Thus, in one or more implementations, each of the elements of FIG. 1 can be standalone or networked devices, or part of a home system. Each separate environment 108 can be controlled differently by one or more control systems 106. The difference can be based on the expected occurrence of the user 109 within the specific environment. Alternatively, a humidifier module 102 may cover several different environments 108, such as different rooms in a building or different compartments in a vehicle (car, train, plane, ship, etc.). In this case, the change of the output (humidification, dehumidification, warm or hot air) can be based on parameters measured by sensors (e.g., sensors 130 (130a and 130b)) that are local for the respective environment, where the target user 109 is. Changing the output of the humidifier module 102 in such a case may be done by redirecting the airflow carrying the humidifier module 102's output from one room/compartment to another, by way of closing and opening different sets of vents.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 116 (FIG. 1) to manually initiate or terminate the sleep session.

Figure 3:
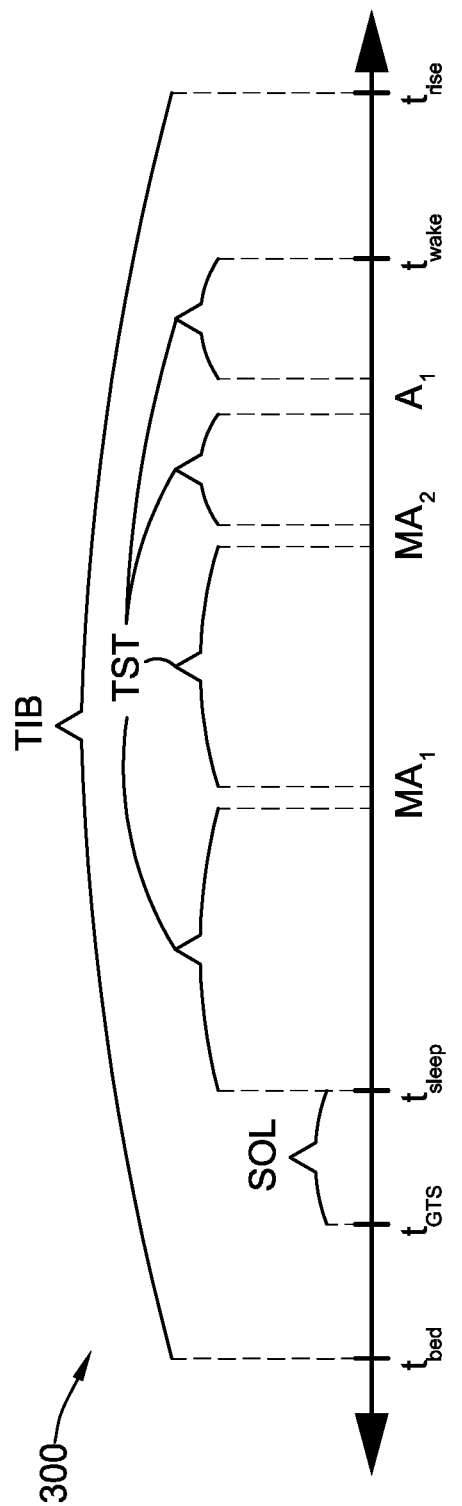
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time toed is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 116, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed (going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings there between. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
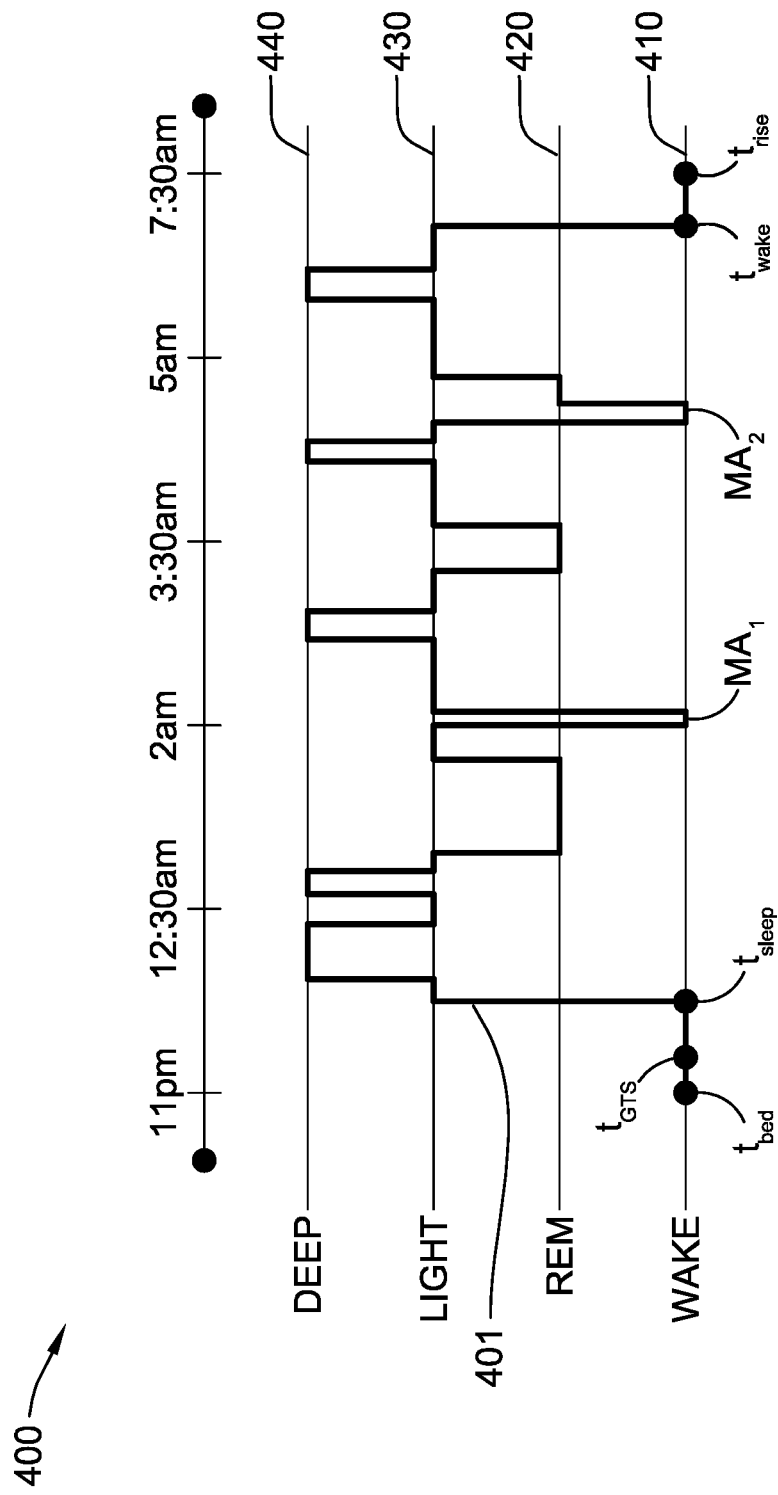
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based at least in part on physiological data associated with the user (e.g., generated by one or more of the sensors 130 described herein). The sleep-wake signal can be indicative of one or more sleep stages, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement there between. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time a the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time bed can be determined based at least in part on, for example, data generated by the motion sensor 138, the microphone 140, the camera 150, or any combination thereof. The go-to-sleep time can be determined based at least in part on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the user device 116 (e.g., data indicative of the user no longer using the user device 116), data from the pressure sensor 132 and/or the flow rate sensor 134 (e.g., data indicative of the user turning on the respiratory device 122, data indicative of the user donning the user interface 124, etc.), or any combination thereof.

Continuous positive airway pressure (CPAP) systems are often used to treat individuals suffering from sleep-related respiratory disorders. Generally, the user of a CPAP system wears a user interface (such as a mask), which delivers pressurized air from a respiratory device into the throat of the user to aid in preventing the airway from narrowing and/or collapsing during sleep, thereby increasing the user's oxygen intake. Many CPAP systems generate audible noise during use that can interfere with or interrupt the user's sleep. This noise often arises from the operation of a motor within the respiratory device that generates the pressurized air. Further, noise can arise from air leaks in CPAP systems (e.g., from a mask of the CPAP system). Detecting and canceling such noises during operation of the CPAP system is useful in aiding users and their bed partners to have high quality sleep that is not interrupted by such noises.

As discussed above, the respiratory therapy system 120 may include a humidifier 129 configured to output moisture into the airflow to the user 210, such as via conduit 126 connected to a user interface 128 that couples to the airway (e.g., mouth and/or nose) of the user 210. As described further below, the humidifier module 102 and the humidifier 129 can work in conjunction to alleviate usage of the humidifier 129. In one or more implementations, the respiratory therapy system 120 may lack the humidifier 129 altogether. In one or more implementations, the respiratory therapy system 120 can be configured to provide positive airway pressure (PAP) treatment for sleep disorder breathing (SDB) conditions, or to provide non-invasive ventilation (NIV). The control system 110 can adjust humidity levels to maximize comfort and efficacy of NIV, when NIV humidification is not provided.

Figure 5:
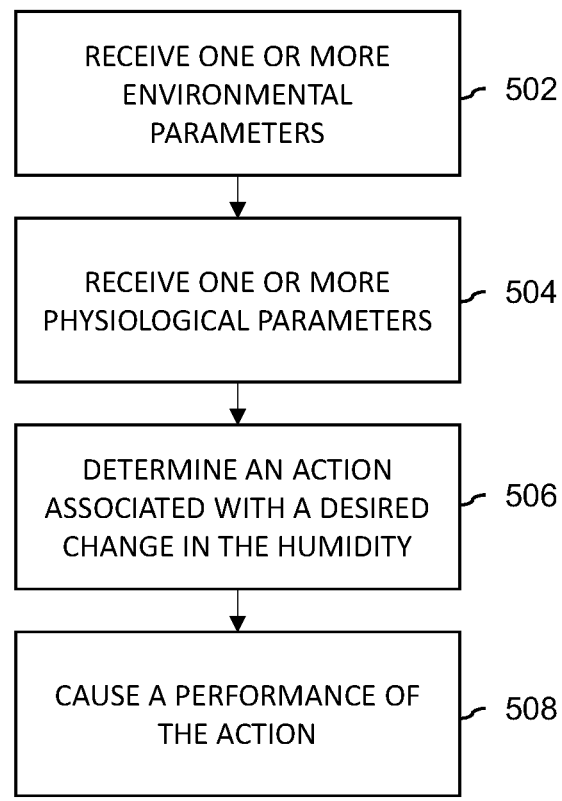
FIG. 5 is a process flow diagram for a method of providing a personalized humidification level, according to some implementations of the present disclosure.

Referring to FIG. 5, a method 500 for providing a personalized humidification level is illustrated. One or more of the steps of the method 500 described herein can be implemented using one or elements of FIG. 1, such as the humidifier module 102, the control system 110, the memory device 114, and one or more sensors 130 (e.g., a first sensor 130a and a second sensor 130b).

At step 502, the control system 110 receives, from the first sensor 130a, one or more environmental parameters regarding conditions of the environment 108. The one or more environmental parameters can include temperature, barometric pressure, air quality, wind chill, a location, or any other environmental parameter disclosed herein, and combinations thereof. In one or more implementations, the one or more environmental parameters can be audio information associated with the environment 108.

At step 504, the control system 110 receives, from the second sensor 130b, one or more physiological parameters associated with the user 109 within the environment 108. The physiological parameters can be any of the physiological parameters disclosed herein and/or combinations thereof. In one or more implementations, the one or more physiological parameters can be audio information associated with the user. The audio information can be information on one or more sounds that correlate to breathing rate, breathing depth, breathing quality, coughing, wheezing, whistling, snoring, or a combination thereof. In one or more implementations, detection of respiration can occur as described in International Patent Application Publication Nos. WO 2007/143535 and WO 2018/050913, which are hereby incorporated by reference herein in their entireties.

Additionally, or in the alternative, the one or more physiological parameters can include heart rate, body temperature, activity level, hydration level, one or more sounds generated by the user, or a combination thereof, including any other physiological condition that can relate to the respiration condition of the user 109.

In one or more implementations, the environment 108 can include one or more other users, besides the user 109. The control system 110 can be configured to determine that the user 109 is a more vulnerable person relative to the one or more other users within the environment 108. For example, the user 109 can be the more vulnerable person based, at least in part, on having an asthma attack, a coughing fit, chronic obstructive pulmonary disease, or another respiratory condition. Thus, the control system 110 can configure itself to match the requirements of the most vulnerable person in terms of breathing issues, i.e., the settings (such as target RH) would be optimized to the person already having, or most likely to have, a breathing issues such as an asthma attack, coughing fit, COPD exacerbation, or other respiratory illness.

In one or more implementations, the system 100 can include the user device 116 associated with the user 109. The control system 110 can receive one or more physiological parameters of the user 109 from the user device 116. The one or more physiological parameters from the user device 116 can include the age, the gender, the body mass index, one or more medical conditions, one or more preexisting conditions, or a combination thereof of the user 109. For example, the "most likely to have breathing issues" estimate discussed previously in the text can be based on the one or more physiological parameters provided by the user as subjective information provided via the user interface of the user device 116.

At step 504, the control system 110 can optionally receive from the user device 116 one or more other physiological parameters associated with the user 109 within the environment 108. The other physiological parameters can be any of the other physiological parameters discussed above with respect to the user device 116, such as age, weight, and how the user is feeling. In one or more implementations, all available parameters can be made available to the control system 110 and input into a classifier, in order for the determination below at step 506 to be made.

At step 506, the control system 110 determines an action associated with a desired change in the humidity within the environment 108 based, at least in part, on the one or more environmental parameters and the one or more physiological parameters. In one or more implementations, the action can be a location change of the humidifier module 102 within the environment 108. In such an implementation, the control system 110 can process the one or more environmental parameters and the one or more physiological parameters to determine a position of the humidifier module 102 relative to the user 109 within the environment 108. The location change can be based on the position of the humidifier module 102 relative to the user 109. In one or more implementations, the action can be indicating to the user to move the humidifier module based on the location change caused by a recommendation outputted by the control system 110. The output can be visual, such as on a display associated with the control system 110 and/or the humidifier module 102. The output can be audible, such as output from a speaker associated with the control system 110 and/or the humidifier module 102.

In one or more implementations, the humidifier module 102 can include one or more fans that direct moisture outputted for changing the humidity. The determined action can include determining to vary the speed and/or the direction of the one or more fans to direct a humidified flow of air in a specific direction. The specific direction can be determined relative to the user 109, relative to the bounds of the environment 108, or a combination thereof. In one or more implementations, the one or more fans can be controlled to provide ventilation to the environment 108, either with or without providing humidity. In the case where the humidifier module 102 is part of a commercial heating, ventilation and/or air conditioning system, the above mentioned relocation of the humidifier module 102 may equivalently be effected by redirecting moisture/cold or heat from one area (part of a passenger's compartment in a vehicle, part of a room or a building, etc.) to another area, such as by opening and closing different sets of vents directing the hot/cold/dry/humid air.

At step 508, the control system 110 causes, at least in part, a performance of the action associated with the change in the humidity in the environment based, at least in part, on moisture outputted by the humidifier module 102. The action can be adjusting the set point of the humidifier module 102 so as to change the humidity in the environment according to an optimal humidity for the user. Based on the physiological parameters, the optimal humidity can benefit the current condition of the user 109, such as benefit the user 109 currently suffering from a cold or other respiratory illness.

In one or more implementations, the control system 110 can further identify an effect of a change in the humidity based on the one or more physiological parameters of the user. The control system 110 can create a feedback loop where steps 504, 506, and 508 can repeat so as to find the optimal conditions based on changes in the physiological conditions, as further discussed below with respect to FIG. 7.

In one or more implementations, the control system 110 can receive one or more meteorological parameters indicative of conditions of the area 118 outside of the environment 108 of the user 109, such as outside the user 109's house. The control system 110 can further determine one or more optimal conditions for the humidifier module 102 based on the one or more environmental parameters and the one or more meteorological parameters. In this case, the action can be changing the humidification output based, at least in part, on the optimal conditions. This allows the humidity value to be targeted somewhere between an ideal level for the user 109 and the outside environment 118 if the control system 110 determines that the user 109 is likely to go outside (or to another area that is not under control of the humidifier module 102). Therefore, the control system 110 can target a personalized ideal level using an adaptive approach for both the environment and the area 118 outside of the environment 108. For example, the user 109's optimal level for respiratory wellness can be 45% RH and outside can be 80% RH. The control system 110 can gradually change (e.g., increase) humidification output to bring the humidity up to the outside level such as to reduce the shock of the change. This may be accompanied by a change in temperature (heating or cooling), or reduction in air purification level (e.g., reducing fan rate).

In one or more implementations, the determination that the user is going to leave the environment 108 can be done based on a statistical model, or interfacing with an electronic diary/calendar of the user 109, or based on the user 109's input.

In one or more implementations, the control system 110 can communicate a personally preferable set of settings to the humidifier module 102 within an environment 108 when the user 109 is going to enter or exit an environment 108. For example, the humidifier module 102 can be within an automotive air conditioning system that has a humidification control function and a wired or wireless interface connected to a network for which to communicate with the control system 110. Alternatively, the humidifier module 102 can be a standalone unit that is connected to a power supply in the vehicle with a communications function. This allows the user 109 to have settings that minimize his or her risk of a disease exacerbation both at home and on the move. In one or more implementations, the control system 110 can activate the humidification function prior to the user 109 entering the vehicle (such as in an electric car that allows the systems to run before the user enters the vehicle).

In one or more implementations, the action of step 508 can be to adjust humidity in the environment 108 (e.g., through the humidifier module 102) and/or humidity generated by the humidifier 129 of the respiratory therapy system 120 to achieve a desired physiological state of the user 109. The physiological state of the user 109 can relate to a desired comfort level that is related to and/or affected by the humidity. The desired comfort level can be a general or default comfort level associated with the user 109. Alternatively, the comfort level can be tied to a specific condition of the user 109 or a specific period of time. For example, the specific condition of the user 109 can be when the user has a cold, is suffering from allergies, has a fever, etc. The humidity in the environment 108 or generated by the humidifier 129 can be controlled by the action of step 508 to achieve a desired physiological state related to, for example, a respiratory state, such as breathing rate, coughing, or other respiratory distress; a stress response, such as galvanic skin response or heart rate variability; dryness of airways, such as nostrils (e.g., provided via user feedback); sleep state; sleep stage, etc. For example, the user 109 may have a cold, and the action of step 508 can be to control the humidity in the environment 108 to improve the breathing rate of the user 109 and/or to reduce the coughing rate or amount of the user 109. The user can then be in a more comfortable state by having less respiratory distress.

Figure 6:
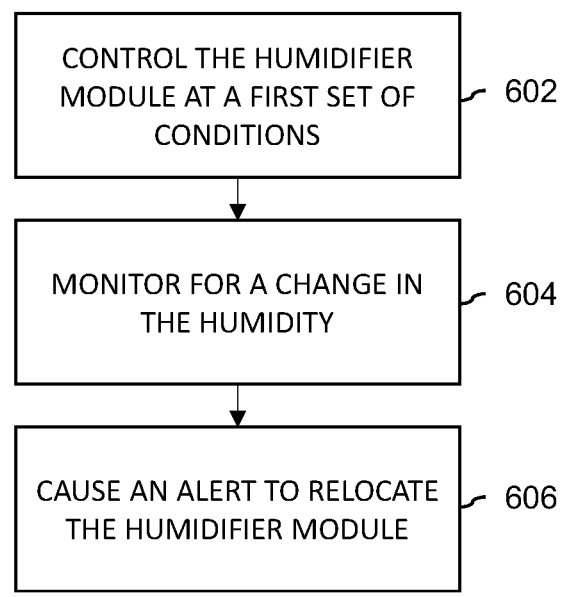
FIG. 6 is a process flow diagram for a method of providing smart humidification, according to some implementations of the present disclosure.

Referring to FIG. 6, a method for providing smart humidification is provided. One or more of the steps of the method 600 described herein can be implemented using one or elements of FIG. 1, such as the humidifier module 102, the control system 110, the memory device 114, and one or more sensors 130 (e.g., a first sensor 130*a* and a second sensor 130*b*).

At step 602, the control system 110 controls the humidifier module 102 at a first set of conditions. The first set of conditions can be based on, for example, a set point for the humidity in the environment 108. The set point can be based on the detected humidity and the temperature and/or a predetermined humidification settings provided by the user.

At step 604, the control system 110 monitors for a change in the humidity in the environment 108 in response to the operation of the humidifier module 102 based on the first set of conditions. The monitoring may lead to a determination of whether the humidifier module 102 is located in a location within the environment 108 so as to effect a change in humidity. The effect on the change in the humidity may be affected by many variables, which can be dependent on the location of the humidifier module 102 in the environment 108.

In one or more implementations, there are one or more sensors 130 located in the environment, such the first sensor 130*a* and the second sensor 130*b*. The monitoring can include receiving information from at least one of the one or more sensors 130 indicative of the change in the humidity. The control system 110 can further receive location information from at least one of the one or more sensors 130 (e.g., sensors 130*a* and 130*b*) indicative of a location of the humidifier module 102 relative to the one or more sensors 130 or to the user 109. The location information can also be based on the location of the humidifier module 102 relative to the bounds of the environment 108, such as the walls of the room.

In one or more implementations, the control system 110 can receive sound information from one or more sound sensors 130 within the environment 108 configured to detect sound. The sound information can include information indicative of a location of a user 109 within the environment 108, such as the breathing discussed above. In response, the control system 110 can process the sound information to determine a location of the humidifier module 102 within the environment 108 relative to the user 109. Further, the control system 110 can determine a new location where to relocate the humidifier module 102 based, at least in part, on the sound information. In one or more implementations, the new location can be relative to the user. A decision on the relocation of the humidifier module 102 may be based on the user 109 spending at least a predetermined amount of time at an alternative location. Relocating the humidifier module 102 may be effected by, for example, sending a message to the user 109 to move the humidifier module 102, or in the case of a mobile humidifier, sending an instruction to a system responsible for moving the humidifier module 102 around. "Relocating" the output of the humidifier module 102 in the case of multi-room or multi-compartment environment may be done by redirecting the airflow carrying the humidifier module 102's output from one room/compartment to another, by way of closing and opening different sets of vents.

At step 606, the control system 110 causes, at least in part, an alert to relocate the humidifier module 102 within the environment 108 based, at least in part, on the monitoring for the change in the humidity. In one or more implementations, the alert can simply be to move the humidifier module 102 without specifying where within the environment 108. In which case, the method of FIG. 6 can stop or repeat until no alert is generated.

In one or more implementations, the alert can include instructions on a location for where to move the humidifier module 102. The location can be relative to the environment 108 based, for example, on information received by the control system 110 that is processed to determine the location of the humidifier module 102 within the environment 108. Alternatively, the location can be relative to the user 109 based, for example, on information processed by the control system 110 to determine the location of the humidifier module 102 relative to a user 109. The information processed to determine the location relative to the user can by the one or more physiological parameters discussed above with respect to FIG. 5. For example, the control system 110 can determine if the humidifier module 102 is too close or too far to the user 109 based on sound generated by the user 109 and the humidifier module 102. Accordingly, the method of FIG. 6 allows a user 109 to position the humidifier module 102 in a more ideal location within the environment 108 to better control or affect the humidity within the environment 108. International Patent Application Publication No. WO 2018/050913 discloses further detail on determining a distance to an object based on sound, the contents of which are hereby incorporated by reference herein in its entirety.

In one or more implementations, similar to step 508 discussed above, the determination of the effect on the user can be to achieve a desired physiological state of the user 109. The specific condition of the user 109 can be when the user has a cold, is suffering from allergies, has a fever, etc. One or more operating conditions of the humidifier module 102 and/or the humidifier 129 can be adjusted to effect a change in the humidity of the environment 108, where the change in the environment 108 is to improve a physiological state of the user 109. For example, the humidity in the environment 108 or generated by the humidifier 129 can be controlled to improve the breathing rate, coughing, or other respiratory distress state of the user.

In one or more implementations, the desired physiological state of the user 109 in the context of the method of FIG. 6, or in the context of any method disclosed herein, can be a desired sleep state (e.g., awake or sleep) or a desired sleep stage (e.g., N1, N2, REM, etc.), as discussed above for FIGS. 3 and 4. The humidity within the environment 108 and/or generated by the humidifier 129 can be controlled to achieve desired sleep states and/or sleep stages throughout one or more sleep sessions. The first and second sets of the one or more physiological parameters of the user in steps 602 and 606 can be associated with detecting the sleep state and/or sleep stage of the user 109. The adjustment of the one or more operating conditions of the humidifier module 102 and/or the humidifier 129 can be to effect a change in the humidity of the environment for achieving a desired sleep state (e.g., asleep) and/or a desired sleep stage (e.g., REM or N3) or a desired pattern of sleep stages through a portion of a sleep session or the entire sleep session.

Figure 7:
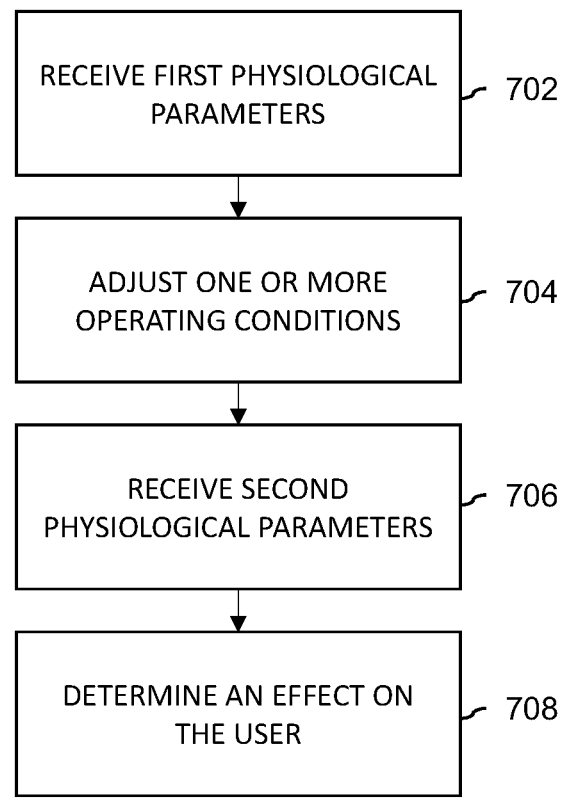
FIG. 7 is a process flow diagram for a method of optimizing a personalized humidification level, according to some implementations of the present disclosure.

Referring to FIG. 7, a method for optimizing a personalized humidification level is provided. One or more of the steps of the method 700 described herein can be implemented using one or elements of FIG. 1, such as the humidifier module 102, the control system 110, the memory device 114, and one or more sensors 130 (e.g., a first sensor 130a and a second sensor 130b).

At step 702, the control system 110 receives, from one or more sensors 130, such as the second sensor 130b, a first set of one or more physiological parameters associated with the user 109 within the environment 108. In one or more implementations, the one or more physiological parameters can include one or more respiratory parameters from the respiratory therapy system 120. The first set of one or more physiological parameters can be used to define a baseline or starting point for optimizing a personalized humidification level.

At step 704, the control system 110 adjusts one or more operating conditions of the humidifier module 102 to effect a change in the humidity of the environment 108. The change in the humidity of the environment 108 is within a predefined range. The adjustment of the one or more operating conditions is to bring the humidity within the environment 108 to a more optimal condition for the user 109 based on the received first set of one or more physiological parameters.

At step 706, the control system 110 receives, from the one or more sensors 130, a second set of one or more physiological parameters associated with the user 109 in the environment 108. The one or more physiological parameters can be the same as in step 702, such as the detected breathing rate and the depth of breathing the person.

At step 708, the control system 110 determines an effect on the user 109 in response to the change in the humidity based, at least in part, on a comparison of the first and second set of one or more physiological parameters. The steps 702-708 can be repeated until the physiological parameters are optimized, such as the user showing optimized breathing patterns.

In one or more implementations, the control system 110 causes, at least in part, a change in one or more operating conditions of an user device 116 configured as an air purifier based, at least in part, on the first set of one or more physiological parameters, the second set of one or more physiological parameters, the effect on the user in response to the change in the humidity, or a combination thereof. The combination of control of the air purifier and the humidity can further assist in finding optimal respiratory conditions for the user 109. The described feedback loop of FIG. 7 provides feedback to accelerate the end goal of having the user breathe better.

If one of the users 109 within the environment 108 that is utilizing the smart humidifier is also using a respiratory therapy system 120 with humidifier 129 at night, the humidity settings may be synchronized—such that common settings are used so as to maximize the comfort of the user 109, and minimize the chance of worsening of a respiratory disease. If there is a single user with a respiratory therapy system 120, the control system 110 can receive information of the operation of the respiratory therapy system 120. As a result, the control system 110 can change the humidifier module 102 to a low power or standby mode while the user 109 is on the respiratory therapy system 120, and switch back to a higher power mode when the user 109 is closer to their wake time (i.e., saves water and energy while the user 109 is receiving humidified air via PAP therapy, but prepares the environment 108 towards the target personalized humidity level before the user ends their PAP therapy such that the user does not experience a large step change in humidity.)

One key benefit of personalized humidification of the methods, systems, and devices in conjunction with the respiratory therapy system therapy is to reduce mouth leak, as well as to combat a congested or dry nose or sore throat. When no humidifier 129 is present, the airflow of a respiratory therapy system 120 can overpower the body's ability to heat and humidify air coming in to the user 109's lungs, and cause irritation to the nasal passages, which in turn can cause mouth breathing, and can worsen mouth leak. Where personalized humidification is provided by the methods and systems of the present disclosure, the respiratory therapy system 120 humidification may be omitted or reduced in order to avoid filling a reservoir of the humidifier 129 of the respiratory therapy system 120 as frequently, while still giving the user 109 the required level of comfort (e.g., avoid dry stuffy nose). The control system 110 can also help people to avoid or minimize mouth breathing even when they are not using a respiratory therapy system by increasing breathing comfort, by avoiding a stuffy nose, etc.

Figure 8:
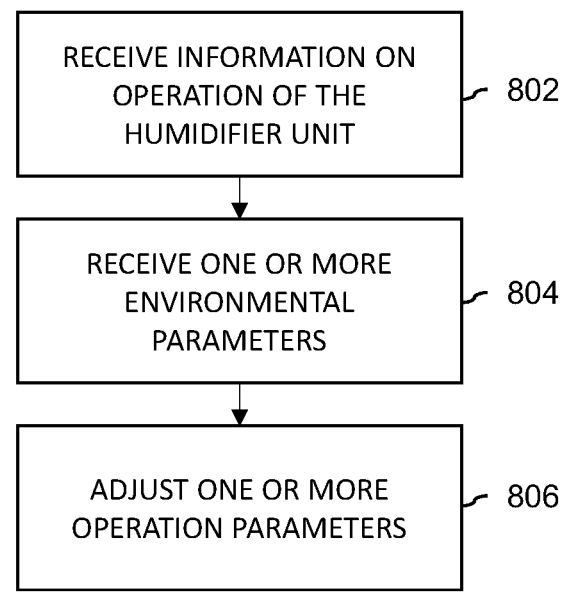
FIG. 8 is a process flow diagram for a method of providing personalized humidification in conjunction with a respiratory therapy system, according to some implementations of the present disclosure.

Referring to FIG. 8, a method for providing personalized humidification in conjunction with a respiratory therapy system is provided. One or more of the steps of the method 800 described herein can be implemented using one or elements of the system 100 of FIG. 1, such as the humidifier module 102, the control system 110, the memory device 114, the respiratory therapy system 120, and one or more sensors 130 (e.g., a first sensor 130*a* and a second sensor 130*b*).

At step 802, the control system 110 receives from respiratory therapy system 120 information on operation of the humidifier 129. The information can include, for example, whether the humidifier 129 is present, is on, the set point, operating conditions, etc.

At step 804, the control system 110 receives, from a first sensor, such as the first sensor 130*a*, one or more environmental parameters regarding conditions of the environment 108 of the respiratory therapy system 120. The environmental parameters can be any of the parameters discussed above, such as humidity, temperature, pressure, etc.

At step 806, the control system 110 adjusts one or more operation parameters of the humidifier 129 or the humidifier module 102, based, at least in part, on the information on operation of the humidifier 129 and the one or more environmental parameters.

In one or more implementations, the control system 110 receives, from a second sensor, such as the sensor 130*b*, one or more physiological parameters associated with the user 109 within the environment 108. The adjustment of the one or more operation parameters can be based, at least in part, on the one or more physiological parameters. The one or more physiological parameters are associated with leak at the user interface 124, and the adjustment of the one or more operation parameters is based on minimizing drying of the user 109's airway based on the leak. In one or more embodiments, the humidifier 129 can be a waterless humidifier. The leak can be detected based on one or more sensors 130 on the respiratory therapy system 120, or the noise generated by the leak at the user interface 124.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system configured to optimize a personalized humidification level comprising:
    a respiratory therapy system configured to provide, via a user interface, an airflow to airways for respiratory treatment, the respiratory therapy system comprising a humidifier unit;
    a humidifier configured to output moisture for changing humidity in an environment of the system;
    memory storing machine-readable instructions; and
    a control system with one or more processors, the one or more processors configured to execute the machine-readable instructions to:
        receive, from one or more sensors, a first set of one or more physiological parameters associated with a user within the environment;
        adjust one or more humidification operating conditions of the humidifier and/or the humidifier unit of the respiratory therapy system to effect change in the personalized humidification level for the user within the environment;
        receive, from the one or more sensors, a second set of one or more physiological parameters associated with the user in the environment;
        determine an effect on the user in response to the change in the one or more humidification operating conditions based, at least in part, on comparing the first set of one or more physiological parameters to the second set of one or more physiological parameters; and
        update the one or more humidification operating conditions based on the determined effect on the user for optimizing the personalized humidification level.

2. The system of claim 1, wherein the first set of one or more physiological parameters defines a baseline for optimizing the personalized humidification level.

3. The system of claim 1, wherein the first set of one or more physiological parameters, the second set of one or more physiological parameters, or a combination thereof comprise at least one respiratory parameter.

4. The system of claim 3, wherein the first set of one or more physiological parameters and the second set of one or more physiological parameters each includes one or more respiratory parameters.

5. The system of claim 4, wherein the one or more respiratory parameters are from the respiratory therapy system.

6. The system of claim 1, wherein the change in the one or more humidification operating conditions is within a predefined range.

7. The system of claim 1, wherein the first set of one or more physiological parameters, the second set of one or more physiological parameters, or a combination thereof are associated with a leak, and the adjustment of the one or more humidification operating conditions is based on minimizing drying caused by the leak.

8. The system of claim 1, wherein the humidifier unit is a waterless humidifier unit.

9. The system of claim 1, wherein at least one of the one or more sensors is located in the respiratory therapy system, at least one of the one or more sensors is located in a user device, or a combination thereof.

10. The system of claim 1, wherein the first set of one or more physiological parameters and the second set of one or more physiological parameters are the same one or more physiological parameters.

11. A method for optimizing a personalized humidification level comprising:

providing, via a user interface of a respiratory therapy system, an airflow to airways for respiratory treatment, the respiratory therapy system comprising a humidifier unit;

outputting moisture, via a humidifier, for changing humidity in an environment of the respiratory therapy system;

receiving, from one or more sensors, a first set of one or more physiological parameters associated with a user within the environment;

adjusting one or more humidification operating conditions of the humidifier and/or the humidifier unit of the respiratory therapy system to effect change in the personalized humidification level for the user within the environment;

receiving, from the one or more sensors, a second set of one or more physiological parameters associated with the user in the environment;

determining an effect on the user in response to the change in the one or more humidification operating conditions based, at least in part, on comparing the first set of one or more physiological parameters to the second set of one or more physiological parameters; and updating the one or more humidification operating conditions based on the determined effect on the user for optimizing the personalized humidification level.

12. The method of claim 11, wherein the first set of one or more physiological parameters defines a baseline for optimizing the personalized humidification level.

13. The method of claim 11, wherein the first set of one or more physiological parameters, the second set of one or more physiological parameters, or a combination thereof comprise at least one respiratory parameter.

14. The method of claim 13, wherein the first set of one or more physiological parameters and the second set of one or more physiological parameters each includes one or more respiratory parameters.

15. The method of claim 14, wherein the one or more respiratory parameters are from the respiratory therapy system.

16. The method of claim 11, wherein the change in the one or more humidification operating conditions is within a predefined range.

17. The method of claim 11, wherein the first set of one or more physiological parameters, the second set of one or more physiological parameters, or a combination thereof are associated with a leak, and the adjustment of the one or more humidification operating conditions is based on minimizing drying caused by the leak.

18. The method of claim 11, wherein the humidifier unit is a waterless humidifier unit.

19. The method of claim 11, wherein at least one of the one or more sensors is located in the respiratory therapy system, at least one of the one or more sensors is located in a user device, or a combination thereof.

20. The method of claim 11, wherein the first set of one or more physiological parameters and the second set of one or more physiological parameters are the same one or more physiological parameters.

* * * * *